United States Patent
Kimura

(10) Patent No.: US 10,895,522 B2
(45) Date of Patent: Jan. 19, 2021

(54) PARTICLE ANALYSIS METHOD FOR IDENTIFYING INFECTIONS

(71) Applicant: SYSMEX CORPORATION, Kobe (JP)

(72) Inventor: Konobu Kimura, Hyogo (JP)

(73) Assignee: SYSMEX CORPORATION, Kobe (JP)

( * ) Notice: Subject to any disclaimer, the term of this patent is extended or adjusted under 35 U.S.C. 154(b) by 250 days.

(21) Appl. No.: 16/003,262

(22) Filed: Jun. 8, 2018

(65) Prior Publication Data

US 2018/0356328 A1    Dec. 13, 2018

(30) Foreign Application Priority Data

Jun. 9, 2017   (JP) ................................. 2017-114237

(51) Int. Cl.
*G01N 15/10*   (2006.01)
*G01N 21/17*   (2006.01)
(Continued)

(52) U.S. Cl.
CPC ......... *G01N 15/10* (2013.01); *G01N 15/1459* (2013.01); *G01N 21/17* (2013.01);
(Continued)

(58) Field of Classification Search
CPC ............... G01N 15/10; G01N 15/1459; G01N 2015/008; G01N 2015/1006;
(Continued)

(56) References Cited

U.S. PATENT DOCUMENTS 4,850,024 A * 7/1989 Motoike ............ G01N 15/1468
382/134
2003/0030784 A1   2/2003 Narisada et al.
(Continued)

FOREIGN PATENT DOCUMENTS

EP   2735859 A2   5/2014
EP   3141885 A1   3/2017

OTHER PUBLICATIONS

The Communication pursuant to Article 94(3) EPC dated Nov. 29, 2019 in a counterpart European patent application No. 18176262.6.
(Continued)

*Primary Examiner* — Jennifer Wecker
(74) *Attorney, Agent, or Firm* — Sughrue Mion, PLLC

(57) ABSTRACT

Disclosed is a particle analysis method for identifying infections, comprising:
step A of irradiating light on a measurement sample prepared by mixing a test blood specimen containing particles, collected from a subject, a fluorescent dye that stains a nucleic acid, and a hemolytic agent, thereby acquiring scattered light and fluorescence from each particle contained in the measurement sample,
step B of specifying particles that are substantially not contained in blood of control subjects not suffering from infection and are determined to be neutrophils contained in blood of patients with infection, based on the scattered light and the fluorescence, and acquiring particle number information on the specified particles, and
step C of determining whether the test blood specimen is a specimen collected from patients with bacterial infection or a specimen collected from patients with viral infection, based on the particle number information.

20 Claims, 10 Drawing Sheets

(52) U.S. Cl.
CPC ......... *G01N 33/52* (2013.01); *G01N 33/569* (2013.01); *G16H 50/30* (2018.01); *G01N 2015/008* (2013.01); *G01N 2015/1006* (2013.01); *G01N 2015/1402* (2013.01); *G01N 2015/1486* (2013.01); *G01N 2015/1488* (2013.01); *G01N 2021/1744* (2013.01)

(58) Field of Classification Search
CPC ... G01N 2015/1402; G01N 2015/1486; G01N 2015/1488; G01N 2021/1744; G01N 21/17; G01N 33/52; G01N 33/569; G16H 50/30
See application file for complete search history.

(56) References Cited

U.S. PATENT DOCUMENTS

| | | | |
|---|---|---|---|
| 2010/0184061 A1* | 7/2010 | Kataoka | G01N 33/56972 435/6.12 |
| 2010/0273168 A1* | 10/2010 | Krockenberger | G01N 33/492 435/6.12 |
| 2012/0282601 A1* | 11/2012 | Abe | G01N 35/026 435/6.1 |
| 2013/0101996 A1 | 4/2013 | Kono et al. | |
| 2014/0147837 A1 | 5/2014 | Kimura et al. | |
| 2014/0234952 A1* | 8/2014 | Moore | G01N 21/6486 435/288.7 |
| 2015/0369793 A1 | 12/2015 | Kimura et al. | |
| 2017/0074863 A1 | 3/2017 | Masuda et al. | |

OTHER PUBLICATIONS

Communication, dated Jan. 23, 2020, issued by the European Patent Office in Application No. 18176262.6.

Sysmex White Paper: "Novel haematological parameters for rapidly monitoring the immune system response", Haematology, Sysmex Europe GmbH, Mar. 13, 2017, pp. 1-5.

The Communication pursuant to Article 94(3) EPC dated Jun. 5, 2019 in a counterpart European patent application No. 18176262.6.

* cited by examiner

PARTICLE ANALYSIS METHOD FOR IDENTIFYING INFECTIONS

CROSS REFERENCE TO RELATED APPLICATIONS

This application claims priority from prior Japanese Patent Application No. 2017-114237, filed on Jun. 9, 2017, entitled "PARTICLE ANALYSIS METHOD FOR IDENTIFYING INFECTIONS", the entire contents of which are incorporated herein by reference.

TECHNICAL FIELD

The present invention relates to a particle analysis method for identifying infections, a particle analyzer for identifying infections, and a computer program for particle analysis for identifying infections.

BACKGROUND

It is known that neutrophils respond to bacterial infection and lymphocytes respond to viral infection. Differences in reactivity of cells to these pathogens are used to identify whether they are bacterial infections or viral infections in patients with high fever.

For example, it is described in White Paper: Novel haematological parameters for rapidly monitoring the immune system response, Sysmex Europe GmbH Release: 13 Mar. 2017 that counts of activated lymphocytes (AS-LYMP (antibody-synthesizing lymphocytes) and RE-LYMP (total reactive lymphocytes)) are markedly increased by viral infection more than bacterial infection. It is described in White Paper: Novel haematological parameters for rapidly monitoring the immune system response, Sysmex Europe GmbH Release: 13 Mar. 2017 that activated neutrophils (NEUT-RI and NEUT-GI) can be used for detection of bacterial infection.

Furthermore, US 2013/0,101,996 A describes a technique for detecting activated neutrophils by bacterial infection or the like using flow cytometry.

SUMMARY

The scope of the present invention is defined solely by the appended claims, and is not affected to any degree by the statements within this summary.

It is important to identify whether a subject is suffering from a bacterial infection or a viral infection in determining a treatment strategy. However, in order to strictly identify whether it is a bacterial infection or a viral infection, a bacterial culture period for a certain period is necessary for a bacterial infection. Further, for a definite diagnosis of viral infection, additional inspection other than white blood cell counting such as PCR method is necessary, and it requires time and expense to diagnose.

In recent years, the appearance of multidrug resistant bacteria due to the frequent use of antibiotics is a problem in medical institutions, thus the use of antibiotics should be minimized in order to reduce the appearance of multidrug resistant bacteria as much as possible. Also, antibiotics are not effective against viruses, so administration of antibiotics to patients with viral infection is not therapeutic.

In patients with fever, rapid and easy diagnose whether they have bacterial infection or viral infection at an appropriate timing, especially when the patients visit a medical institution for the first time after developing a fever, has great merit that treatment policy can be decided at an early stage of the infection. In particular, the inspection initially performed as a routine for a patient complaining of fever symptoms is counting of the number of white blood cells, an inspection for classification of white blood cells into four types or classification of white blood cells into five types. Thus, in this inspection, the ability to identify whether the subject suffers from bacterial infection or suffers from viral infection can alleviate patient's own physical and economic burdens, and furthermore, brings about the public benefit of minimizing the appearance of multidrug resistant bacteria.

The first embodiment that is a means of solving the problem of the present invention is a particle analysis method for identifying infections, including step A of irradiating light on a measurement sample prepared by mixing a test blood specimen containing particles, collected from a subject, a fluorescent dye that stains a nucleic acid, and a hemolytic agent, thereby acquiring scattered light and fluorescence from each particle contained in the measurement sample, step B of specifying particles that are substantially not contained in blood of control subjects not suffering from infection and are determined to be neutrophils contained in the blood of patients with infection, based on the scattered light and the fluorescence, and acquiring particle number information on the specified particles, and step C of determining whether the test blood specimen is a specimen collected from patients with bacterial infection or a specimen collected from patients with viral infection, based on the particle number information.

A second embodiment that is a means of solving the problem of the present invention is a particle analyzer 50 for identifying infections, including a light source 201 for irradiating light on a measurement sample prepared by mixing a test blood specimen containing particles, collected from a subject, a fluorescent dye that stains a nucleic acid, and a hemolytic agent, a detection unit 13 for receiving scattered light and fluorescence from each particle contained in the measurement sample generated by the irradiation, and a processing unit 21 for specifying particles that are substantially not contained in blood of control subjects not suffering from infection and are determined to be neutrophils contained in blood of patients with infection, based on the scattered light and the fluorescence, and acquiring particle number information on the specified particles, and determining whether the test blood specimen is a specimen collected from patients with bacterial infection or a specimen collected from patients with viral infection, based on the particle number information.

A third embodiment that is a means of solving the problem of the present invention is a computer program for particle analysis for identifying infections which makes a computer execute a step of irradiating light on a measurement sample prepared by mixing a test blood specimen containing particles, collected from a subject, a fluorescent dye that stains a nucleic acid, and a hemolytic agent, thereby acquiring scattered light and fluorescence from each particle contained in the measurement sample, a step of specifying particles that are substantially not contained in blood of control subjects not suffering from infection and are determined to be neutrophils contained in blood of patients with infection, based on the scattered light and the fluorescence, and acquiring particle number information on the specified particles, and a step of determining whether the test blood specimen is a specimen collected from patients with bacterial infection or a specimen collected from patients with viral infection, based on the particle number information.

According to the first to third embodiments of the present invention, it is possible to easily identify whether the specimen is a specimen collected from patients with bacterial infection or a specimen collected from patients with viral infection, using a device for automatic classification of white blood cells into four types or automatic classification of white blood cells into five types usually used in medical institutions.

DETAILED DESCRIPTION OF THE PREFERRED EMBODIMENTS

[1. Particle Analysis Method for Identifying Infections]
[1-1. Overview]

The first embodiment relates to a particle analysis method for identifying infections that determines whether a blood specimen collected from a subject (test blood specimen) is a specimen collected from patients with bacterial infection or a specimen collected from patients with viral infection.

Figure 1:
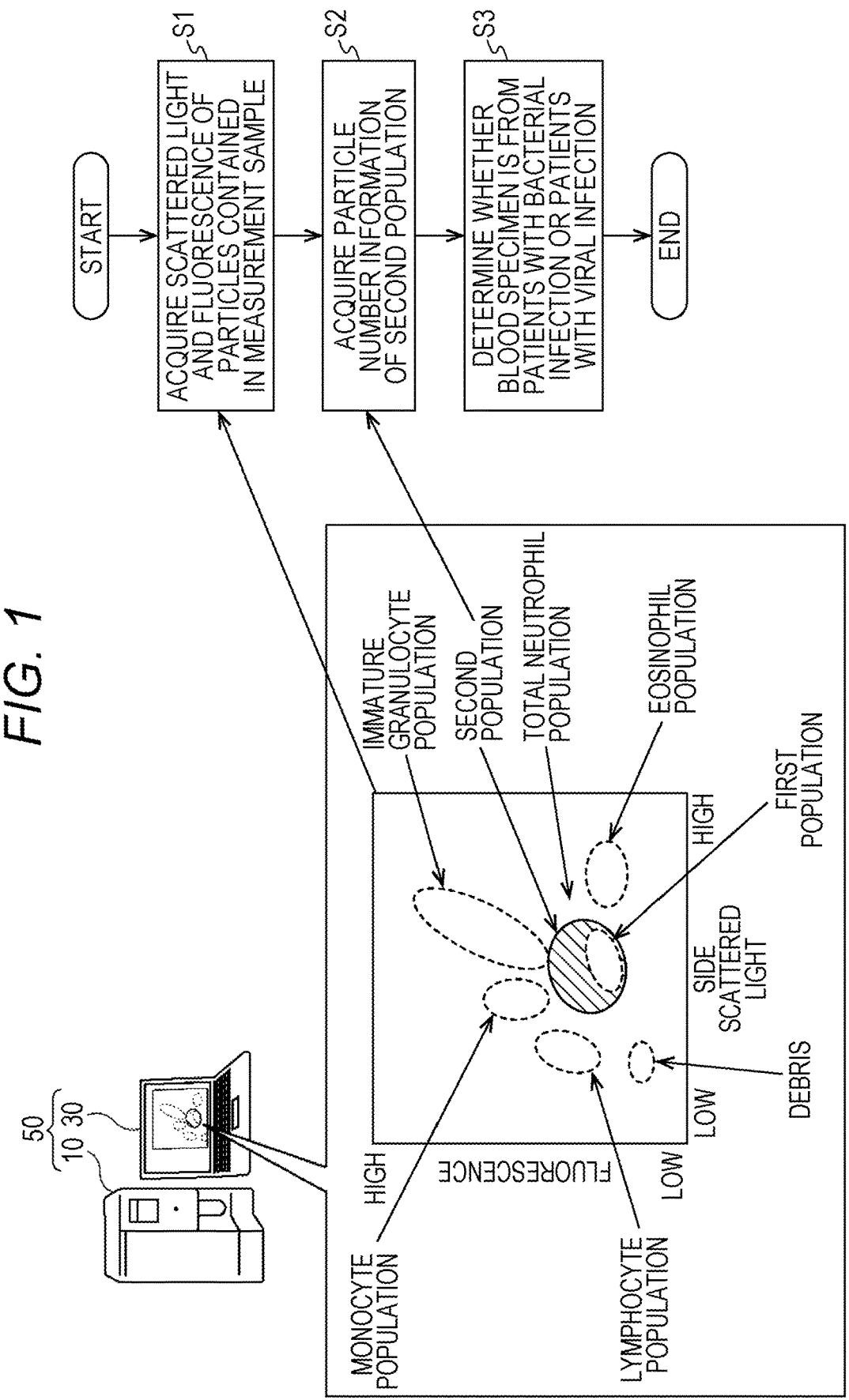
FIG. 1 is a diagram showing an overview of the present invention and an example of a method for determining a second population.

The overview of the first embodiment is shown in FIG. 1.

Specifically, the first embodiment includes at least the following step A (Step S1), step B (Step S2), and step C (Step S3).

The step A (Step S1) of the first embodiment acquires scattered light and fluorescence obtained by irradiating light on a measurement sample containing particles, prepared by mixing a test blood specimen, a fluorescent dye that stains at least a nucleic acid, and a hemolytic agent.

The step B (Step S2) of the first embodiment specifies particles that are not substantially contained in the blood of control subjects not suffering from infection and are determined to be neutrophils contained in the blood of patients with infection, based on the scattered light intensity and the fluorescence intensity acquired in the step A (Step S1). Then, particle number information on the specified particles is acquired. The particle number information on the specified particles corresponds to the particle information of the second population described later.

The step C (Step S3) of the first embodiment determines whether the test blood specimen is a specimen collected from patients with bacterial infection or a specimen collected from patients with viral infection, based on the particle number information.

In the first embodiment, the bacterium is not limited as long as it is a pathogenic bacterium to humans. Preferably, from the bacteria, obligate intracellular parasitic bacteria (*mycoplasma, chlamydia, rickettsia*, etc.) and acid-fast bacteria group are excluded.

In the first embodiment, the virus is not limited as long as it is a virus that is pathogenic to humans.

[1-2. Preparation of Measurement Sample]

In the first embodiment, the subject is not particularly limited, and examples thereof include a person having inflammatory symptoms such as fever.

The blood specimen is not limited as long as it is the state that counting of the number of white blood cells and classification of white blood cells are possible. The blood is preferably peripheral blood. For example, examples of the blood include peripheral blood collected using an anticoagulant such as ethylenediamine tetraacetate (sodium salt or potassium salt) or sodium heparin. Peripheral blood may be collected from an artery or from a vein.

In the first embodiment, the particle is not limited as long as it is derived from a blood specimen. The particles are preferably cells, more preferably nucleated cells, further preferably blast cells, nucleated cells other than myelocytes before metamyelocytes and megakaryocytes.

Preparation of a measurement sample is not limited as long as a nucleic acid of particles contained in a blood specimen is stained with a fluorescent dye and red blood cells contained in the blood specimen are prepared to be hemolyzable using a hemolytic agent.

Examples of the fluorescent dye that stains a nucleic acid (hereinafter sometimes simply referred to as "fluorescent dye") include propidium iodide, ethidium bromide, ethidium-acridine heterodimer, ethidium diazide, ethidium homodimer-1, ethidium homodimer-2, ethidium monoazide, trimethylenebis[[3-[[4-[[(3 thylbenzothiazol-3-ium)-2-yl]methylene]-1,4-dihydroqui nolin]-1-yl]propyl]dimethylaminium]*tetraiodide (TOTO-1), 4-[(3-methylbenzothiazol-2 (3H)-ylidene)methyl]-1-[3-(trimethylaminio)propyl] quinolin ium*diiodide (TO-PRO-1), N,N,N',N'-tetramethyl-N,N'-bis[3-[4-[3-[(3-methylbenzothiazol-3-ium)-2-yl]-2-propeny lidene]-1,4-dihydroquinolin-1-yl]propyl]-1,3-propanediaminium*tetraiodide (TOTO-3), 2-[3-[[1-[3-(trimethylaminio)propyl]-1,4-dihydroquinolin]-4-ylidene]-1-propenyl]-3-me thylbenzothiazol-3-ium*diiodide (TO-PRO-3), and fluorescent dyes represented by the following general formula (I). Among them, the fluorescent dyes represented by the following general formula (I) are preferable.

[Chemical formula 1]

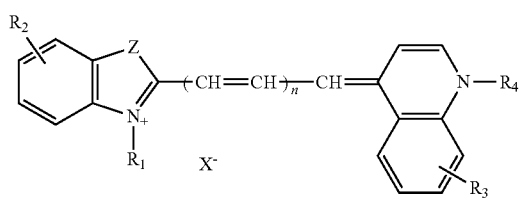

(I)

wherein $R_1$ and $R_4$ are a hydrogen atom, an alkyl group, an alkyl group having a hydroxy group, an alkyl group having an ether group, an alkyl group having an ester group or a benzyl group that may have a substituent; $R_2$ and $R_3$ are a hydrogen atom, a hydroxyl group, a halogen, an alkyl group, an alkenyl group, an alkynyl group or an alkoxy group; Z is a sulfur atom, an oxygen atom or a carbon atom having a methyl group; n is 0, 1, 2 or 3; and $X^-$ is an anion.

In the general formula (I), in a case where either one of $R_1$ and $R_4$ is an alkyl group having 6 to 18 carbon atoms, the other is preferably a hydrogen atom or an alkyl group having less than 6 carbon atoms. The alkyl group having 6 to 18 carbon atoms is preferably an alkyl group having 6, 8 or 10 carbon atoms. Examples of the substituent of the benzyl group of $R_1$ and $R_4$ include alkyl groups having 1 to 20 carbon atoms, alkenyl groups having 2 to 20 carbon atoms and alkynyl groups having 2 to 20 carbon atoms, and a methyl group or an ethyl group is particularly preferable. Examples of the alkenyl group of $R_2$ and $R_3$ include alkenyl groups having 2 to 20 carbon atoms. Examples of the alkoxy group of $R_2$ and $R_3$ include alkoxy groups having 1 to 20 carbon atoms, and a methoxy group or an ethoxy group is particularly preferable. Examples of the anion in $X^-$ include halogen ions such as $F^-$, $Cl^-$, $Br^-$ and $I^-$, $CF_3SO_3^-$, $BF_4^-$, and the like.

The fluorescent dye for staining a nucleic acid may be a solution. The solvent for dissolving the fluorescent dye is not particularly limited, and examples thereof include water, organic solvents, and mixtures thereof. Examples of the organic solvent include alcohol, ethylene glycol, dimethylsulfoxide (DMSO), and the like. The fluorescent dye is preferably dissolved in an organic solvent from the viewpoint of storage stability.

The fluorescent dye capable of staining a nucleic acid is preferably mixed with a blood specimen in the form of a staining reagent containing a buffer solution or the like. The final concentration of the fluorescent dye to be mixed with the blood specimen can be appropriately set depending on the type of the fluorescent dye. For example, the final concentration of the fluorescent dye represented by the general formula (I) is usually 0.01 to 100 µg/L and preferably 0.1 to 10 µg/L. The concentration is preferably 0.2 to 0.6 µg/µL, and particularly preferably 0.3 to 0.5 µg/µL. As the fluorescent dye, two or more kinds of fluorescent dyes capable of staining a nucleic acid may be used.

As the staining reagent, a commercially available staining reagent for classifying white blood cells can also be used. Examples of the commercially available staining reagent for classifying white blood cells include Stromatolyzer 4DS manufactured by SYSMEX CORPORATION. Stromatolyzer 4DS is a staining reagent containing a fluorescent dye represented by the above general formula (I).

It is preferable that the hemolytic agent is the one that not only hemolyzes red blood cells but also can classify white blood cells in the peripheral blood into at least four subclasses.

By using this hemolytic agent, red blood cells are hemolyzed, the cell membranes of nucleated cells can be damaged, and the nucleic acids in the cells are more likely to be stained by the fluorescent dye.

The hemolytic agent includes anionic surfactants, cationic surfactants, bipolar surfactants, and nonionic surfactants. The surfactant contained in the hemolytic agent may be of one kind or of two or more kinds. When two or more kinds of surfactants are contained, the combination thereof may be a combination of a cationic surfactant and a nonionic surfactant, a combination of cationic surfactants, or a combination of anionic surfactants. Preferably, it is a combination of a cationic surfactant and a nonionic surfactant.

As the cationic surfactant, a quaternary ammonium salt type surfactant or a pyridinium salt type surfactant is preferable. More specific examples include surfactants having 9 to 30 carbon atoms in total represented by a general formula (II) or (III).

[Chemical formula 2]

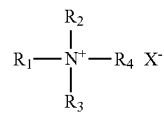

(II)

[Chemical formula 3]

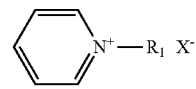

(III)

In the formulas (II) and (III), $R_1$ is an alkyl group or alkenyl group having 6 to 18 carbon atoms, $R_2$ and $R_3$ are an alkyl group or alkenyl group having 1 to 4 carbon atoms, $R_4$ is an alkyl group or alkenyl group having 1 to 4 carbon atoms or a benzyl group, and X is a halogen atom.

As $R_1$, alkyl groups or alkenyl groups having 6, 8, 10, 12, and 14 carbon atoms are preferable, and straight chain alkyl groups are particularly preferable. More specific examples of $R_1$ include an octyl group, a decyl group, and a dodecyl group. As $R_2$ and $R_3$, a methyl group, an ethyl group, and a propyl group are particularly preferable. As $R_4$, a methyl group, an ethyl group, and a propyl group are preferable.

As the nonionic surfactant, diethylene glycol, saponin, or a polyoxyethylene nonionic surfactant represented by the following general formula (IV) and the like are preferable.

It is preferable to use a polyoxyethylene nonionic surfactant represented by

[Chemical formula 4]

(IV)

wherein $R_1$ represents an alkyl, alkenyl or alkynyl group having 8 to 25 carbon atoms; $R_2$ represents O,

[Chemical formula 5]

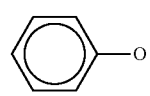

or COO; and n represents an integer of 10 to 50.

Specific examples of the polyoxyethylene nonionic surfactant represented by the above general formula (IV) include polyoxyethylene alkyl ethers, polyoxyethylene sterol, polyoxyethylene castor oil, polyoxyethylene sorbitol fatty acid esters, polyoxyethylene alkyl amines, polyoxyethylene polyoxypropylene alkyl ethers, and the like.

Examples of the anionic surfactant include N-lauroylsarcosinates, glycolates, deoxycholates, and the like.

In the first embodiment, the surfactant may be in the form of a solution. The solvent for dissolving the surfactant is not particularly limited, and examples thereof include water, organic solvents, and mixtures thereof. Examples of the organic solvent include alcohols, ethylene glycol, DMSO, and the like.

In the case of using a surfactant solution, its concentration can be appropriately set depending on the type of surfactant.

In the case of a cationic surfactant, its concentration is usually 10 to 10,000 ppm and preferably 100 to 1,000 ppm, and in the case of a nonionic surfactant, its concentration is usually 10 to 100,000 ppm, preferably 100 to 10,000 ppm, and more preferably 1,000 to 5,000 ppm.

A hemolytic agent can be used as a hemolysis reagent in combination with a component other than the surfactants described above. Examples of components other than the surfactants that can be contained in the hemolysis reagent include alcohols such as methanol, ethanol, and phenoxyethanol, fixing solutions such as formaldehyde, chelating agents, organic acids, buffering agents, and the like.

As the organic acid, an organic acid having at least one aromatic ring in the molecule or a salt thereof is preferable. More specifically, examples thereof include benzoic acid, phthalic acid, hippuric acid, salicylic acid, p-aminobenzenesulfonic acid, benzenesulfonic acid, and salts thereof, and the like.

Examples of the buffering agent include carbonates, citrates, HEPES, phosphates, and the like. As the buffering agent, a buffering agent that keeps the pH of the hemolysis reagent in the range of 4.5 to 11.0 and preferably 5.0 to 9.0 is preferable because it increases the hemolysis efficiency of red blood cells. The pH of the hemolysis reagent can be adjusted by adding a pH regulator such as citric acid, potassium hydrogen carbonate, sodium hydroxide, or hydrochloric acid.

The osmotic pressure of the hemolysis reagent is not particularly limited, and the osmotic pressure is preferably 20 to 150 mOsm/kg, from the viewpoint of effectively hemolyzing red blood cells. The osmotic pressure of the hemolysis reagent can be adjusted by adding an osmotic pressure regulator such as sugar, amino acid, organic solvent or sodium chloride. Examples of the sugar include glucose, xylitol, mannitol, arabinose, ribitol, and the like. Examples of the amino acid include alanine, proline, glycine, valine, and the like. Examples of the organic solvent include ethylene glycol, glycerin, and the like.

Examples of the chelating agent include ethylenediamine tetrahydrochloride and the like.

Specific examples of the hemolysis reagent include an ammonium chloride hemolytic agent (pH 7.3, ammonium chloride 1.68 M, potassium hydrogen carbonate 100 mM, EDTA 2K 0.82 mM), a cell-immobilizing hemolytic agent (pH 7.3, formaldehyde 10%, methanol 3.5%, diethylene glycol 30%, citric acid 100 mM), and a cell membrane permeable hemolytic agent (pH 7.3, phenoxyethanol 1% or less, saponin 1% or less, N-laurylsarcosine sodium salt 1% or less, sodium azide 1% or less).

By using the hemolytic agent or hemolytic reagent, nucleated cells are more likely to be stained with a fluorescent dye, and white blood cells are likely to cause differences in size and the like between lymphocytes, monocytes, eosinophils, and granulocytes other than eosinophils. Therefore, it is possible to classify white blood cells into at least four subclasses based on the scattered light intensity and the fluorescence intensity derived from the particles, and to detect neutrophils having different states.

As the hemolysis reagent, a commercially available hemolysis reagent for classifying white blood cells can also be used. Examples of the commercially available hemolysis reagent for classifying white blood cells include Stromatolizer 4DL manufactured by SYSMEX CORPORATION. Stromatolyzer 4DL is a hemolysis reagent containing the cationic surfactant, the nonionic surfactant, and the organic acid, and has a pH within the above range.

The order of mixing the blood specimen, the fluorescent dye, and the hemolytic agent is not particularly limited. For example, the fluorescent dye and the hemolytic agent may be mixed first, and the mixed solution and the blood specimen may be mixed. The hemolytic agent and the blood specimen may be mixed first, and the mixed solution and the fluorescent dye may be mixed. In the first embodiment, the same result can be obtained regardless of the order of mixing.

It is preferred that mixing of the blood specimen, the staining reagent, and the hemolysis reagent is performed so that the volume ratio of the test blood specimen to the mixture of the staining reagent and the hemolysis reagent is 1:5 to 1:1000 and preferably 1:10 to 1:100. In this case, the ratio of the staining reagent to the hemolysis reagent in the mixture is 1:1 to 1:1000 and preferably 1:10 to 1:100. By mixing the blood specimen, the staining reagent, and the hemolysis reagent at such ratio, hemolysis of red blood cells proceeds promptly, and the white blood cell nucleic acid can be stained. The amount of blood specimen is about 5 to 500 μL that is sufficient for measurement.

In the first embodiment, after mixing the blood specimen, the staining reagent, and the hemolysis reagent, it is preferred that incubation is carried out at a temperature of 15 to 50° C. and preferably 30 to 45° C., for 5 to 120 seconds and preferably 5 to 30 seconds.

[1-3. Acquisition of Scattered Light and Fluorescence]

In the present disclosure, a method for acquiring scattered light and fluorescence is not limited. For example, it is possible to acquire scattered light and fluorescence using the particle analyzer described in the second embodiment described later. Specifically, a data processing unit 20 constituting at least a part of the particle analyzer according to the second embodiment acquires information on scattered light and information on fluorescence, from the information (wavelength, intensity, etc.) on scattered light and fluorescence received by a measurement unit 10. The information on the scattered light and the information on the fluorescence may be any of a pulse width of light, an integrated value or a differential value of the pulse width, a light intensity, and the like. Hereinafter, the first embodiment will be described taking the light intensity as an example, but the present embodiment is not to be construed as being limited to the light intensity. The scattered light intensity and the fluorescence intensity may be acquired as follows: the measurement unit 10 calculates scattered light intensity and fluorescence intensity from the received scattered light and fluorescence and transmits the scattered light intensity and the fluorescence intensity to the data processing unit 20, and the data processing unit 20 receives the scattered light intensity and the fluorescence intensity. Alternatively, the scattered light intensity and the fluorescence intensity may be acquired as follows: the measurement unit 10 transmits information on the received scattered light and fluorescence to the data processing unit 20, and the data processing unit 20 calculates the scattered light intensity and the fluorescence intensity based on the information on each received light.

In the first embodiment, the scattered light is preferably side scattered light and the fluorescence is side fluorescence. The configuration and operation of the data processing unit 20 and the measurement unit 10 will be described in the sections 2. and 3. described later.

[1-4. Classification of Particles and Acquisition of Particle Number Information]

In the first embodiment, the nucleated cells in the blood specimen are classified, based on the scattered light intensity and fluorescence intensity acquired at the beginning.

Specifically, when the measured particles are normal white blood cells, the particles are classified into four groups (clusters) of a lymphocyte population, a monocyte population, an eosinophil population, and a granulocyte population other than eosinophils, based on the scattered light intensity and the fluorescence intensity. Granulocytes other than eosinophils represent neutrophils and basophils. Since the basophils contained in the neutrophil and basophil populations are negligible, the neutrophil and basophil populations can be regarded as a neutrophil population.

In the first embodiment, normal white blood cells may be classified into five groups of lymphocytes, monocytes, neutrophils, eosinophils, and basophils.

In one example of the first embodiment, it is preferable that the classification of white blood cells is performed based on a scattergram obtained by creating a biaxial scattergram with the scattered light intensity on the abscissa and the fluorescence intensity on the ordinate. In this method, the area on the scattergram where each population of lymphocytes, monocytes, neutrophils, eosinophils, and basophils appears is predetermined from the data accumulated for normal white blood cells of control subjects not suffering from infection. Therefore, for example, by creating a scattergram with the side scattered light intensity on the abscissa and the fluorescence intensity on the ordinate, the particles that are normal white blood cells are classified into four groups of lymphocytes, monocytes, neutrophils, and eosinophils, as shown in FIG. 1. Further, by using known analysis software, windows surrounding each group on the scattergram are provided, the number of particles in the windows is counted, and particle number information (the number of particles (concentration) per unit volume, scattered light intensity and fluorescence intensity of each particle, etc.) of each group can be acquired.

As another example of the first embodiment, without creating a scattergram, the range of scattered light intensities and range of fluorescence intensities of each population of lymphocytes, monocytes, neutrophils, eosinophils, and basophils may be preset, and each population may be classified by comparing the scattered light intensity and the fluorescence intensity of each particle in the test blood specimen with the above settings. The classification can be performed using known analysis software.

The total neutrophil population contains neutrophils in various states. For example, in the total neutrophil population, neutrophils of control subjects not suffering from infection (preferably control subjects not having inflammatory symptoms) and neutrophils of patients suffering from infection or the like are included. The range of scattered light intensities and the range of fluorescence intensities in neutrophils of control subjects not suffering from infection can be set by previously measuring blood specimens of one or more control subjects. The range of scattered light intensities and the range of fluorescence intensities in neutrophils of patients suffering from infection can also be set by previously measuring blood specimens of one or more patients suffering from infection. The range of scattered light intensities and the range of fluorescence intensities of total neutrophils can also be set by measuring various blood specimens collected from control subjects, subjects suffering from infection, subjects suffering from other diseases, and the like.

In the first embodiment, a particle population included in the range of scattered light intensities and the range of fluorescence intensities in neutrophils of control subjects not suffering from infection is called as a control neutrophil population. A population of particles contained in the measurement sample of the test blood specimen, that is determined to correspond to the control neutrophil population is also referred to as a first population of the neutrophil population.

It is preferable that the control subject is a person whose ratio of band neutrophils in white blood cells contained in the blood is less than the reference value of band neutrophils. The reference value for band neutrophils is 10% in peripheral blood.

Next, particles that are not substantially contained in the blood of control subjects not suffering from infection and are determined to be neutrophils contained in the blood of patients with infection are specified. Subsequently, particle number information on the specified particles is acquired. In the present specification, the specified population of particles is also referred to as a second population. That is, the particle number information of the specified particles is also the particle number information of the second population described below. The particle number information of the second population can be acquired by any one of the following methods.

An example of a method for acquiring particle number information of the second population is a method for acquiring, as particle number information of the second population, particle number information of a particle population contained in the total neutrophil population and not contained in the first population. More specifically, the value obtained by subtracting the number of particles contained in the first population from the number of particles contained in the total neutrophil population is the number of particles contained in the second population. In this case, between the step A and the step B, step A-1 of acquiring the particle number information of the total neutrophil population for the test blood specimen and the particle number information of the first population, from the scattered light and the fluorescence acquired in the step A, can be included.

Another example of a method for acquiring particle number information of the second population is a method for determining the second population based on the appearance positions of an immature granulocyte population that is a population of immature granulocytes (granulocytic cells before metamyelocytes) and the first population. Specifically, when fluorescence emitted from the particles is acquired, particles that appear at a position where the fluorescence intensity is lower than the appearance position of the immature granulocyte population and appear at a position where the fluorescence intensity is higher than that of the first population are selected. For the particles, the second population can be determined by selecting particles that appear in substantially the same range of scattered light intensities as the first population. Subsequently, particle number information is acquired for the determined second population.

Figure 2:
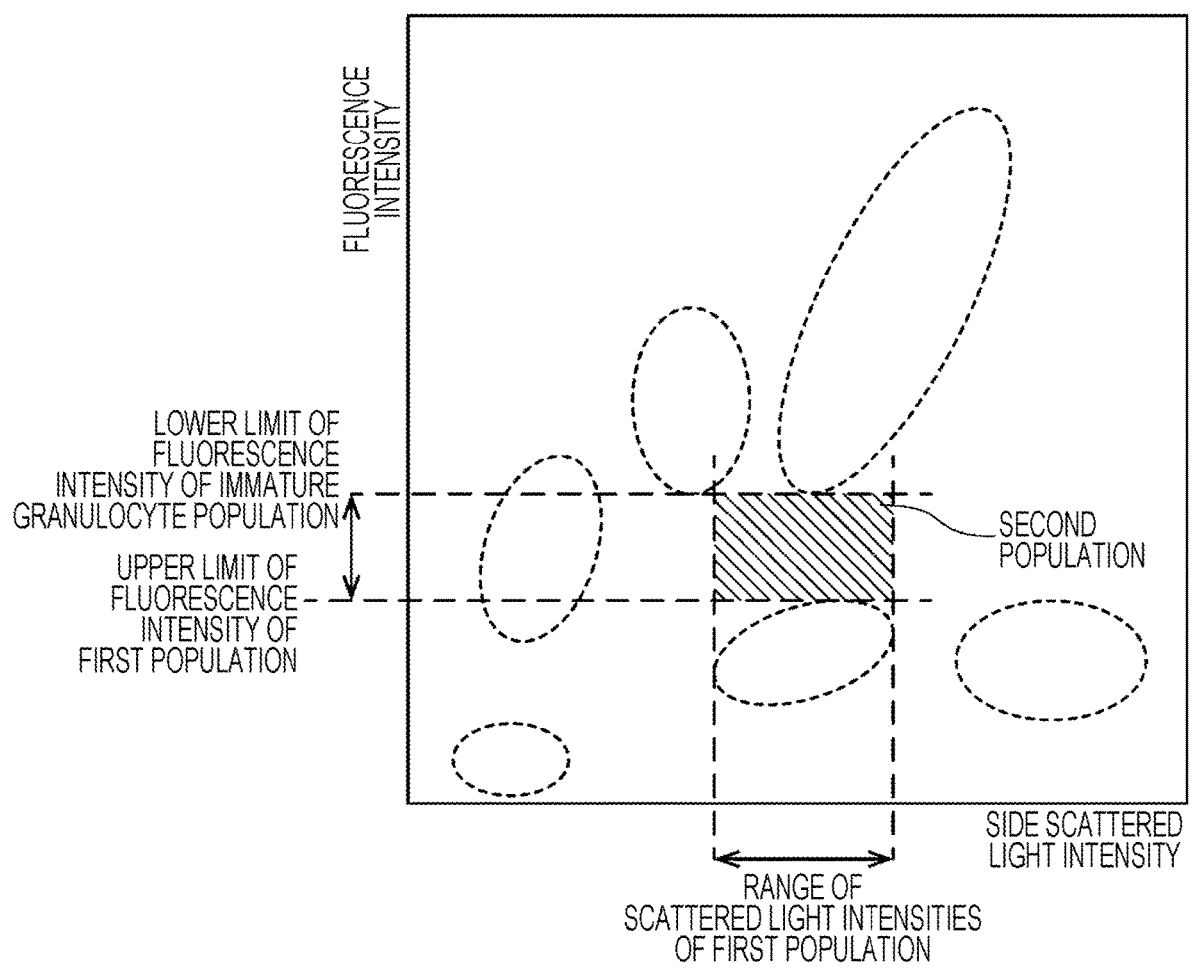
FIG. 2 is a diagram showing another example of a method for determining a second population.

More preferably, it is a range indicated by hatching in FIG. 2. That is, it is a method for acquiring, as particle number information of the second population, particle number information of a particle population in which the fluorescence intensity is between the lower limit of the fluorescence intensity of the immature granulocyte population and the upper limit of the fluorescence intensity of the first population that are predetermined, and the scattered light intensity is in the range of scattered light intensities of the first population. The immature granulocyte population can be determined by previously measuring blast cells, promyelocytes, myelocytes, and peripheral blood including myelocytes, and bone marrow fluid and thereby setting the range of scattered light intensities and the range of fluorescence intensities in which these cells are included.

[1-5. Identification of Infections]

Next, based on the particle number information acquired in 1-4 above, whether the test blood specimen is a specimen collected from patients with bacterial infection or a specimen collected from patients with viral infection is determined.

The determination method can be performed by any one of the following methods.

An example of the determination method is a method for determining based on the ratio between the number of particles included in the particle number information of the white blood cell population and the number of particles included in the particle number information of the second population. Preferably, it is determined based on the ratio of the number of particles in the second population to the number of particles in the white blood cell population, that is, the value obtained by dividing the value of the number of particles in the second population by the value of the number of white blood cells ("the number of particles in the second population"/"the number of white blood cells").

The number of white blood cells can be calculated by a conventional method. For example, particle number information of the white blood cells can be acquired by counting the number of particles whose scattered light intensities fall within a predetermined range. Acquisition of particle number information of the white blood cells can be performed before step C.

The ratio is compared with a separately set threshold value. The threshold value includes a first threshold value for determining whether or not it is a specimen collected from patients with bacterial infection and a second threshold value for determining that it is not a specimen collected from patients with bacterial infection and patients with viral infection. The second threshold value is lower than the first threshold value. More specifically, when the ratio is compared with the first threshold value, and the ratio is higher than the first threshold value, it can be determined that the test blood specimen is a specimen collected from patients with bacterial infection. When the ratio is equal to or less than the first threshold value and higher than the second threshold value, it can be determined that the test blood specimen is a specimen collected from patients with viral infection. When the ratio is equal to or less than the second threshold value, it can be determined that the test blood specimen is not a specimen collected from patients with bacterial infection or patients with viral infection.

The first threshold value and the second threshold value can be preset by a statistical method. For example, for a blood specimen group (bacterial infection group) previously collected from patients with bacterial infection, a blood specimen group (viral infection group) collected from patients with viral infection, and a blood specimen group (control group) collected from control subjects not suffering from infection (preferably control subjects not having inflammatory symptoms), the above ratio is calculated for each blood specimen. Based on the obtained ratio value of each group, a first threshold value capable of identifying the bacterial infection group and the viral infection group, and a second threshold value capable of identifying the viral infection group and the control group are calculated. The method for calculating the threshold value is not particularly limited. Examples of the method for calculating the threshold value include a method using an ROC curve (Receiver Operating Characteristic curve) and the like. In another example, a threshold value that can most accurately classify the group of patients with viral infection, the group of patients with bacterial infection, and the control group, from the viewpoint of sensitivity, specificity, negative predictive value, positive predictive value, and the like, can be set. Examples of another method for setting a threshold value include a discriminant analysis method, a mode method, a Kittler method, a 3σ method, a p-tile method, and the like.

The another example of the determination method is a method for determining based on the ratio of the number of particles included in the particle number information of the total neutrophil population to the number of particles included in the particle number information of the second population, using the particle number information of the total neutrophil population, instead of the number of white blood cells. Preferably, it is a determination method based on the value obtained by dividing the value of the number of particles in the second population by the value of the number of particles in the total neutrophil population ("the number of particles in the second population"/"the number of particles in the total neutrophil population"). In this case, when the test blood specimen is a specimen collected from patients with viral infection, the value of "the number of particles in the second population"/"the number of particles in the total neutrophil population" decreases. When the test blood specimen is a specimen collected from patients with bacterial infection, "the number of particles in the second population"/"the number of particles in the total neutrophil population" approaches 1. Therefore, it is possible to more clearly identify whether the test blood specimen is a specimen collected from patients with bacterial infection or a specimen collected from patients with viral infection.

The another example of the determination method is a method for determining based on the ratio of the number of particles included in the particle number information of the lymphocyte population to the number of particles included in the particle number information of the second population, using the particle number information of the lymphocyte population, instead of the number of white blood cells. Preferably, it is a determination method based on the value obtained by dividing the value of the number of particles in the second population by the value of the number of particles in the lymphocyte population ("the number of particles in the second population"/"the number of particles in the lymphocyte population").

The particle number information of the lymphocyte population can be acquired, for example, based on the scattered light intensity and the fluorescence intensity acquired in the step A, between the step A and the step C.

In addition, the number of particles included in the particle number information of the monocyte population or the number of particles included in the particle number information of the eosinophil population may be used, instead of the number of white blood cells.

[2. Particle Analyzer for Identifying Infections]

The second embodiment relates to a particle analyzer 50 including at least a data processing unit 20. In the second embodiment, the particle analyzer 50 may include a measurement unit 10 in addition to the data processing unit 20. The second embodiment may include a particle analysis system in which the data processing unit 20 and the measurement unit 10 are communicably connected via a network or the like. In the second embodiment, while explanation of the terms already explained in the above section 1. is omitted, explanation of each term in the above section 1. is also applied to the second embodiment.

[2-1. Configuration of Data Processing Unit]

Figure 3:
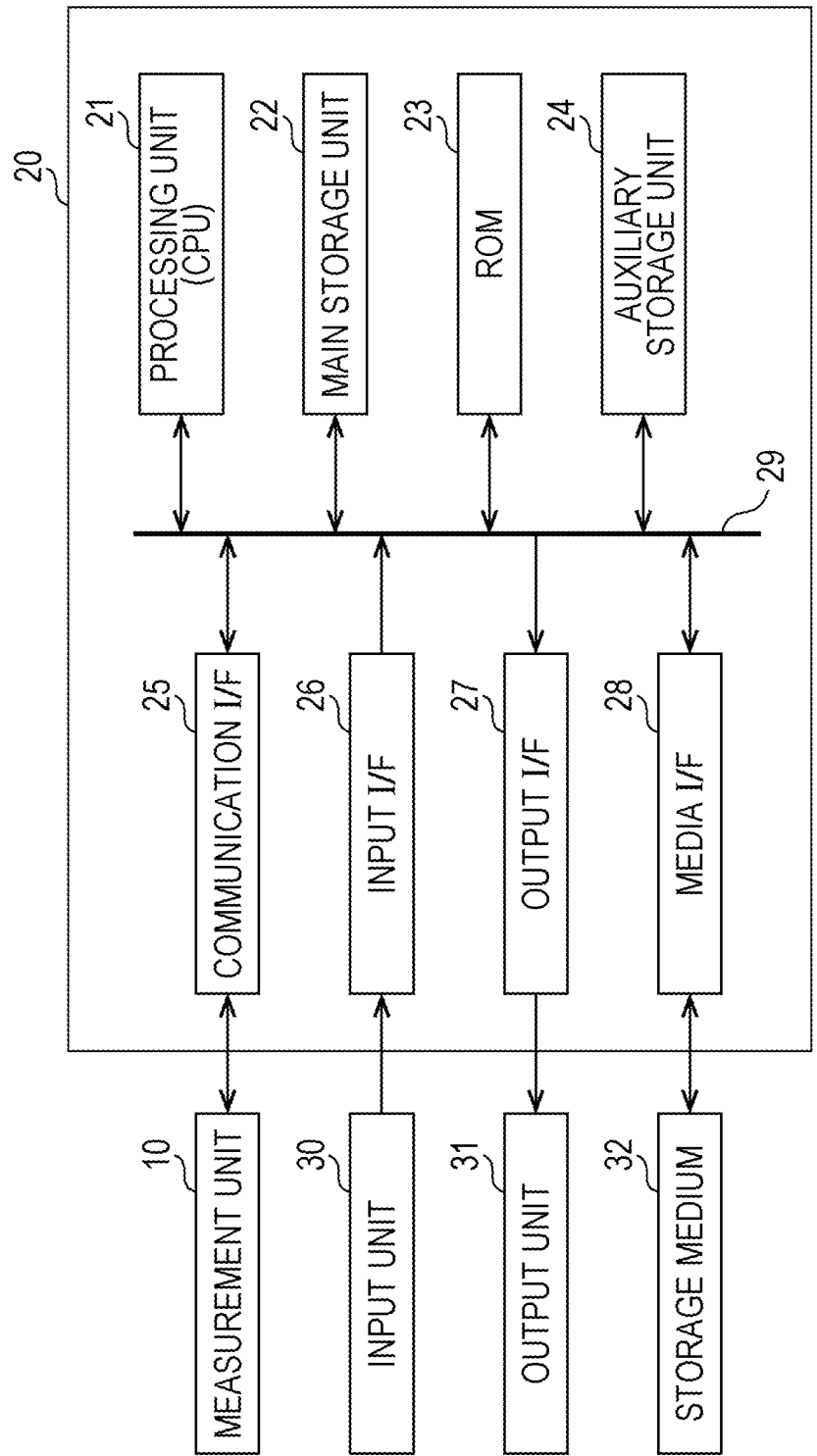
FIG. 3 is a diagram showing a configuration of a data processing unit.

FIG. 3 shows a hardware configuration of the data processing unit 20. The data processing unit 20 may be connected to an input unit 30, an output unit 31, and a storage medium 32.

In the data processing unit 20, a CPU 21, a main storage unit 22, a ROM (read only memory) 23, an auxiliary storage unit 24, a communication interface (I/F) 25, an input interface (I/F) 26, an output interface (I/F) 27, and a media interface (I/F) 28 are data-communicably connected with each other via a bus 29.

The CPU 21 is a processing unit of the data processing unit 20. The CPU 21 executes a computer program stored in the auxiliary storage unit 24 or the ROM 23 and processes data to be acquired so that the data processing unit 20 functions.

The ROM 23 is configured by a mask ROM, a PROM, an EPROM, an EEPROM, and the like, and a computer program executed by the CPU 21 and data used for the computer program are recorded in the ROM 23. The CPU 21 may be an MPU 21. When starting the data processing unit 20, the ROM 23 stores a boot program executed by the CPU 21 and programs and settings related to the operation of the data processing unit 20 hardware.

The main storage unit 22 is configured by a RAM (Random Access Memory) such as SRAM or DRAM. The main storage unit 22 is used for reading the computer program recorded in the ROM 23 and the auxiliary storage unit 24. The main storage unit 22 is used as a work area when the CPU 21 executes these computer programs.

The auxiliary storage unit 24 is configured by a semiconductor memory element such as a hard disk and a flash memory, an optical disk, and the like. In the auxiliary storage unit 24, various computer programs to be executed by the CPU 21, such as operating systems and application programs, and various setting data used for executing computer programs are stored. Specifically, a computer program for particle analysis for identifying infections described later; the range of scattered light intensities and the range of fluorescence intensities for acquiring particle number information of a lymphocyte population, a monocyte population, a total neutrophil population, a control neutrophil population, an eosinophil population or an immature granulocyte population; and a setting values of the first threshold value, the second threshold value, and the like are stored in a nonvolatile manner.

The communication I/F 25 is configured by a serial interface such as USB, IEEE1394 and RS-232C, a parallel interface such as SCSI, IDE, and IEEE1284, an analog interface including a D/A converter and an A/D converter, a network interface controller (Network interface controller: NIC), and the like. Under the control of the CPU 21, the communication I/F 25 receives the data from the measurement unit 10 or another external device, and the communication I/F 25 transmits or displays information stored in or generated by the data processing unit 20 as necessary to the measurement unit 10 or to the outside. The communication I/F 25 may communicate with the measurement unit 10 or another external device via a network.

The input I/F 26 is configured by, for example, a serial interface such as USB, IEEE1394, and RS-232C, a parallel interface such as SCSI, IDE, and IEEE1284, an analog interface including a D/A converter an A/D converter, and the like. The input I/F 26 receives character input, click, voice input and the like from the input unit 30. The received input content is stored in the main storage unit 22 or the auxiliary storage unit 24.

The input unit 30 is configured by a touch panel, a keyboard, a mouse, a pen tablet, a microphone, and the like. The input unit 30 performs character input or voice input to the data processing unit 20. The input unit 30 may be connected from the outside of the data processing unit 20 or integrated with the data processing unit 20.

The output I/F 27 is configured by, for example, the same interface as the input I/F 26. The output I/F 27 outputs the information generated by the CPU 21 to the output unit 31. The output I/F 27 outputs the information generated by the CPU 21 and stored in the auxiliary storage unit 24 to the output unit 31.

The output unit 31 is configured by, for example, a display, a printer, and the like. The output unit 31 displays the measurement results transmitted from the measurement unit 10, various operation windows in the data processing unit 20, analysis results, and the like.

The media I/F 28 reads, for example, application software or the like stored in the storage medium 32. The read application software or the like is stored in the main storage unit 22 or the auxiliary storage unit 24. The media I/F 28 writes the information generated by the CPU 21 in the storage medium 307. The media I/F 28 writes the information generated by the CPU 21 and stored in the auxiliary storage unit 24 to the storage medium 32.

The storage medium 32 is configured by a flexible disk, CD-ROM, DVD-ROM, or the like. The storage medium 32 is connected to the media I/F 28 by a flexible disk drive, a CD-ROM drive, a DVD-ROM drive, or the like. In the storage medium 32, an application program or the like for allowing the computer to execute operation may be stored.

The CPU 21 may acquire application software and various settings necessary for controlling the data processing unit 20 via a network, instead of reading from the ROM 23 or the auxiliary storage unit 24. The application program is stored in the auxiliary storage unit of the server computer on the network, and it is also possible that the data processing unit 20 accesses the server computer to download the computer program and store it in the ROM 23 or the auxiliary storage unit 24.

In the ROM 23 or the auxiliary storage unit 24, an operation system for providing a graphical user interface environment such as Windows (registered trademark) manufactured and sold by Microsoft Corporation is installed. It is assumed that the application program according to the second embodiment operates on the operating system. That is, the data processing unit 20 may be a personal computer or the like.

[2-2. Configuration of Measurement Unit]

Figure 4:
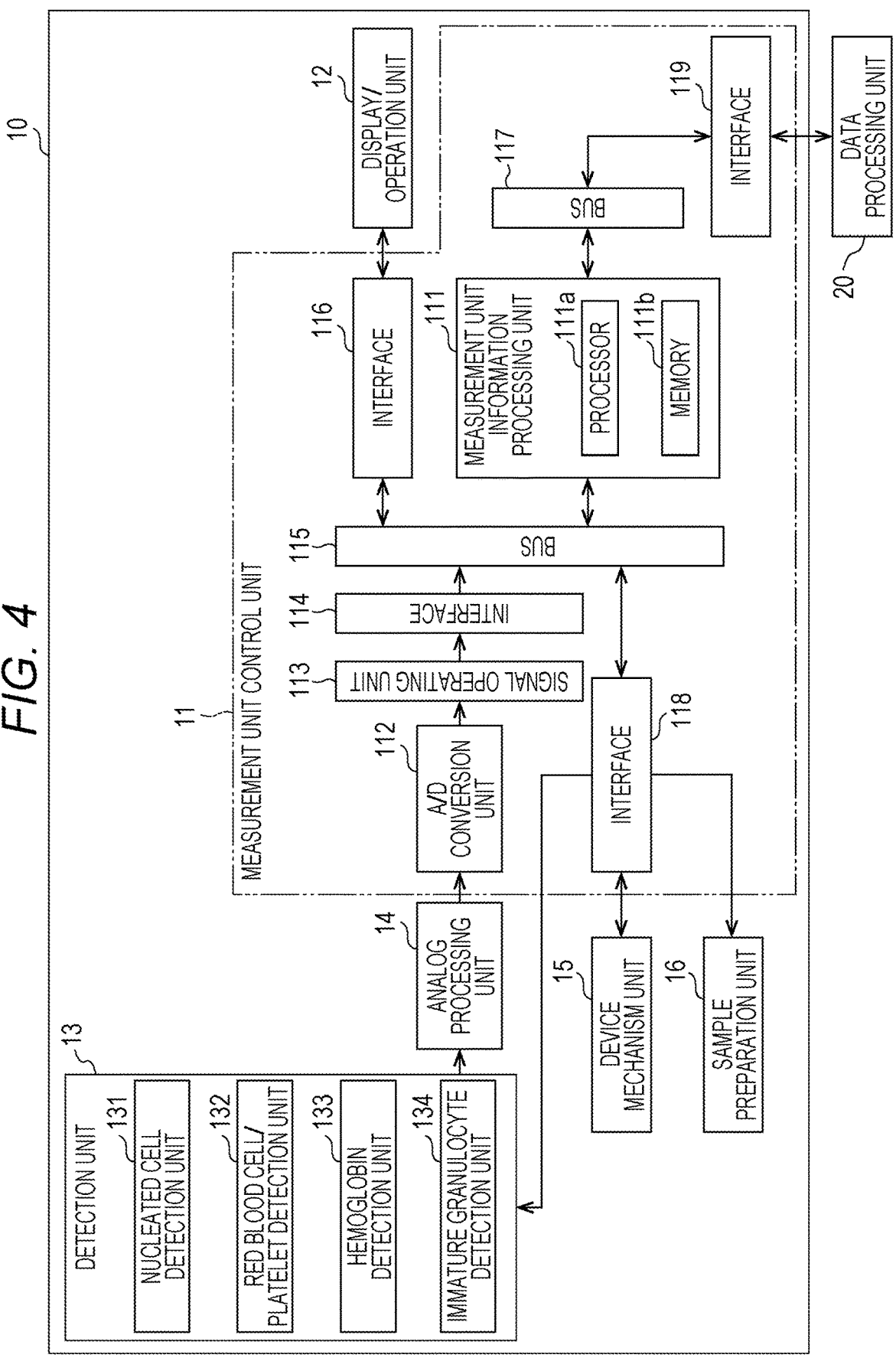
FIG. 4 is a diagram showing a configuration of a measurement unit.
Figure 5:
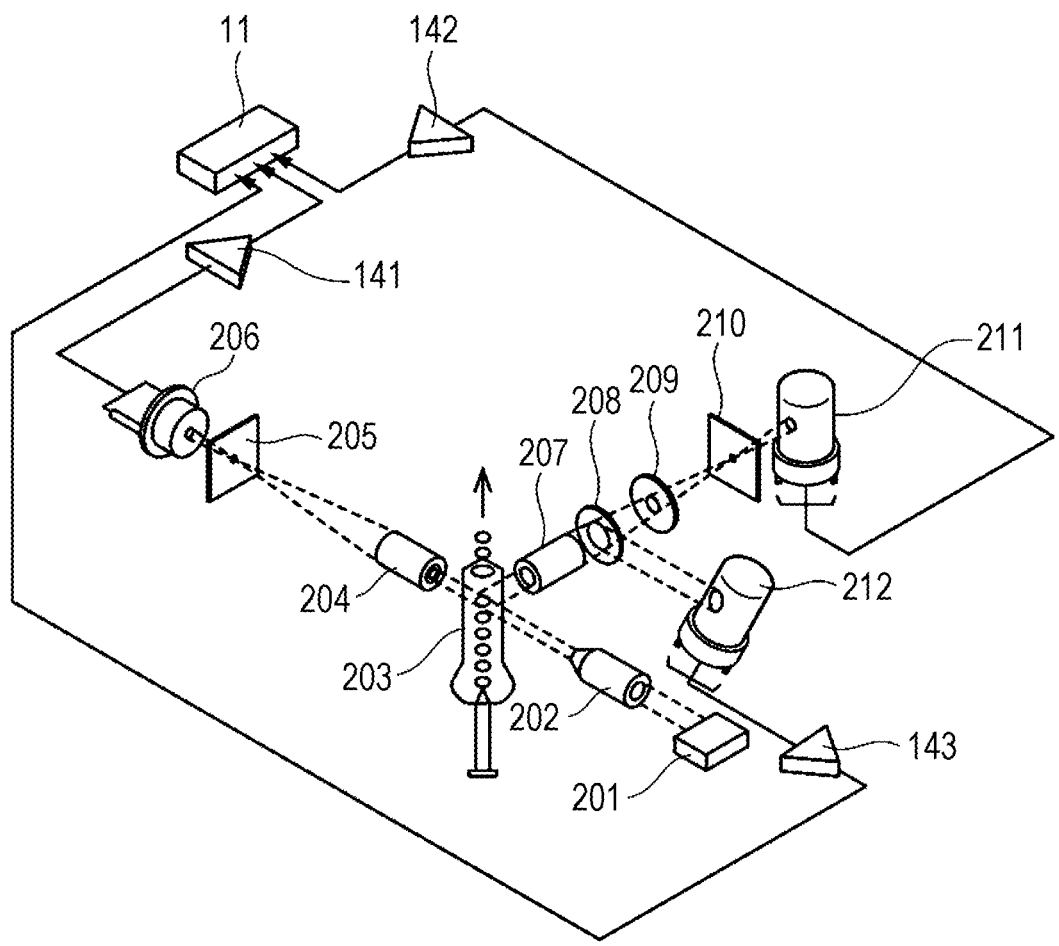
FIG. 5 is a diagram showing a configuration of a nucleated cell detection unit.
Figure 6:
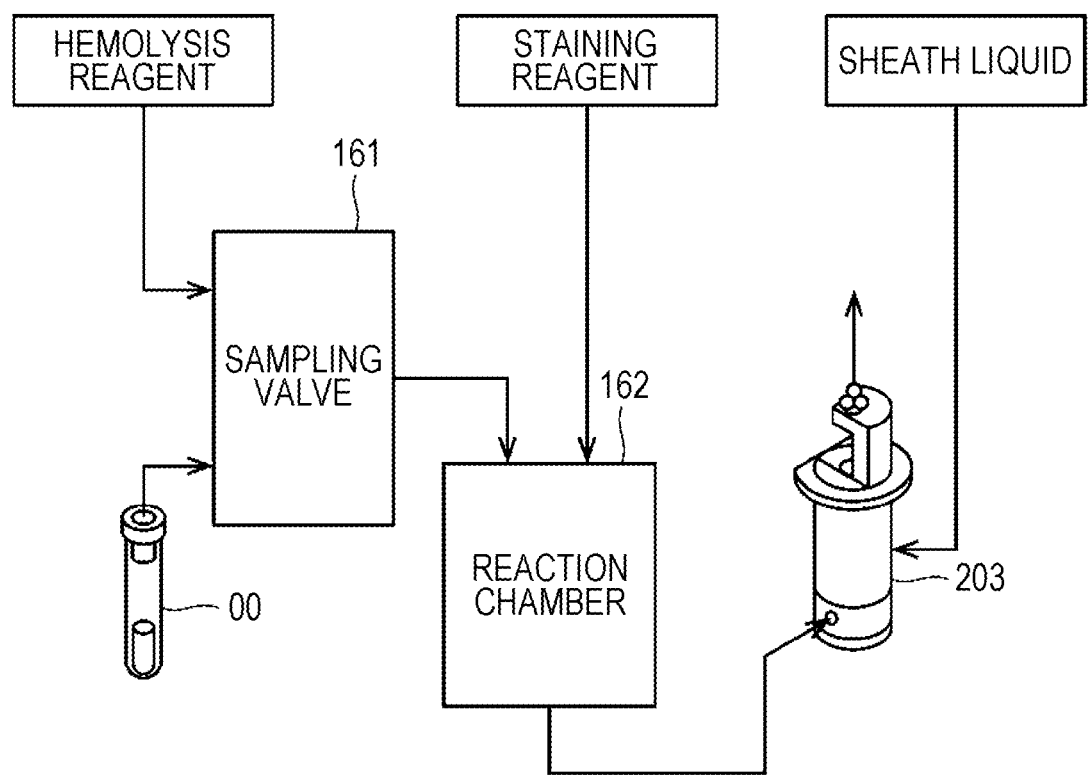
FIG. 6 is a diagram showing a configuration of a sample preparation unit.

With reference to FIGS. 4 to 6, the configuration of the measurement unit 10 will be described.

The measurement unit 10 irradiates light onto a measurement sample prepared according to the method described in 1-2. above and measures scattered light and fluorescence generated from the particles in the sample.

In the second embodiment, the measurement unit 10 is preferably a flow cytometer. In the measurement by the flow cytometer, when the particles contained in the measurement sample pass through a flow cell (sheath flow cell) 203 provided in the flow cytometer, a light source 201 irradiates the flow cell 203 with light, and scattered light and fluorescence emitted from the particles in the flow cell 203 by this light are detected.

In the second embodiment, scattered light is not particularly limited as long as it is scattered light that can be measured by a flow cytometer which is generally distributed. Examples of the scattered light include forward scattered light (for example, in the vicinity of a light receiving angle of 0 to 20 degrees) and side scattered light (in the vicinity of a light receiving angle of 90 degrees). It is known that side scattered light reflects internal information such as cell nuclei and granules and forward scattered light reflects cell size information. In the second embodiment, it is preferable to measure the side scattered light as the scattered light intensity.

Fluorescence is light obtained by measuring excited fluorescence emitted from nucleic acids or the like stained with a fluorescent dye in cells when excitation light of an appropriate wavelength is irradiated to a measurement sample. The excitation light wavelength and the light reception wavelength can be appropriately selected depending on the type of fluorescent dye used.

FIG. 4 shows a block diagram of the measurement unit 10. As shown in the figure, the measurement unit 10 includes a detection unit 13 for detecting blood cells, an analog processing unit 14 for the output of the detection unit 13, a measurement unit control unit 11, a display/operation unit 12, and a device mechanism unit 15.

The detection unit 13 includes at least a nucleated cell detection unit 131 for detecting nucleated cells such as white blood cells, a red blood cell/platelet detection unit 132 for measuring the number of red blood cells and the number of platelets, and a hemoglobin detection unit 133 for measuring the amount of hemoglobin in the blood. The detection unit may include an immature spherule detection unit 134 for detecting immature spherules such as immature granulocytes as an arbitrary configuration. The nucleated cell detection unit 131 is configured by an optical detection unit, and more specifically includes a configuration for performing detection by a flow cytometry method.

FIG. 5 shows a configuration of the optical system of the nucleated cell detection unit 131. In this figure, light emitted from a laser diode as a light source 201 is irradiated to particles passing through the flow cell 203 via an irradiation lens system 202.

In the second embodiment, the light source 201 of the flow cytometer is not particularly limited, and a light source 201 having a wavelength suitable for exciting a fluorescent dye is selected. As such light source 201, for example, a semiconductor laser including a red semiconductor laser and a blue semiconductor laser, a gas laser such as an argon laser and a helium-neon laser, a mercury arc lamp or the like is used. Especially, semiconductor lasers are preferable because they are very inexpensive compared with gas lasers.

As shown in FIG. 5, forward scattered light emitted from particles passing through the flow cell 203 is received by a photodiode (forward scattered light receiving element) 206 via a condenser lens 204 and a pinhole section 205. The side scattered light is received by a photomultiplier (side scattered light receiving element) 211 via a condenser lens 207, a dichroic mirror 208, a band pass filter 209, and a pinhole section 210. The side fluorescence is received by a photomultiplier (side fluorescent light receiving element) 212 via a condenser lens 207 and a dichroic mirror 208.

Light receiving signals output from the light receiving units 206, 211, and 212 are subjected to analog processing such as amplification and waveform processing by the analog processing unit 14 having the amplifiers 141, 142, and 143, respectively, and are sent to the measurement unit control unit 11.

As shown in FIG. 4, the measurement unit control unit 11 includes an A/D conversion unit 112, a signal operating unit 113 for performing a predetermined operation processing on a digital signal output from the A/D conversion unit 112, and a measurement unit information processing unit 111 including a processor 111a and a memory 111b for operating the processor 111a. The measurement unit control unit 11 includes an interface unit 116 interposed with the display/operation unit 12 and an interface unit 118 interposed with the device mechanism unit 15.

The signal operating unit 113 is connected to the measurement unit information processing unit 111 via an interface unit 114 and a bus 115. The measurement unit information processing unit 111 is connected to the detection unit 13 and the device mechanism unit 15 via the interface units 116 and 118 and the bus 115, and is connected to the data processing unit 20 via an interface unit 119 and a bus 117.

The A/D conversion unit 112 converts a light receiving signal output from the analog processing unit 14 into a digital signal, and outputs it to the signal operating unit 113. The signal operating unit 113 performs a predetermined operation processing on the digital signal output from the A/D conversion unit 112. Then, the signal operating unit 113 outputs the operation result (measurement result) to the measurement unit information processing unit 111 via the interface unit 114 and the bus 115.

The measurement unit information processing unit 111 is connected to the data processing unit 20 via the external interface unit 119, and can transmit the operation result output from the signal operating unit 113 to the data processing unit 20. The measurement unit information processing unit 111 controls a device mechanism unit 15 including a sampler (not shown) for automatically supplying sample containers, a fluid system for preparing and measuring samples, and performs other controls.

The measurement unit 10 may include a sample preparation unit 16 for preparing a measurement sample according to the method described in 1-2. above. The sample preparation unit 16 is controlled by the measurement unit information processing unit 111 via the interface 118 and the bus 115. FIG. 6 shows a state in which a blood specimen, a staining reagent, and a hemolysis reagent are mixed to prepare a measurement sample in the sample preparation unit 16 provided in the measurement unit 10, and the obtained measurement sample is measured by the nucleated cell detection unit.

In FIG. 6, the blood specimen in a sample container 00 is sucked from a suction pipette (not shown) to a sampling valve 161. The blood specimen quantified by the sampling valve 161 is mixed with a predetermined amount of the hemolysis reagent, and the obtained mixture is conveyed to a reaction chamber 162. A predetermined amount of the staining reagent is supplied to the reaction chamber 162 and mixed with the above mixture. By allowing the mixture of the blood specimen and the staining reagent and the hemolysis reagent to react in the reaction chamber 162 for a predetermined time, the red blood cells in the blood specimen are hemolyzed, and a measurement sample in which nucleated cells are stained with a fluorescent dye is obtained.

The obtained measurement sample is sent to the flow cell 203 in the nucleated cell detection unit 131 together with a sheath liquid (for example, CELLPACK (II), manufactured by SYSMEX CORPORATION), and is measured by the flow cytometry method in the nucleated cell detection unit 131.

[2-4. Operation of Particle Analyzer for Identifying Infections]

Next, with reference to FIG. 7 and FIG. 8, the operation of the particle analyzer for identifying infections in the second embodiment will be described. The operation of the particle analyzer is controlled by the CPU 21 (processing unit 21) of the data processing unit 20, in accordance with a computer program for identifying infections described later.

Initially, the processing unit 21 receives an input for starting acquisition of scattered light intensity and fluorescence intensity of each particle generated by the measurement unit information processing unit 111, from the input unit 30 to the data processing unit 20 by an inspector (Step S01).

Next, the processing unit 21 acquires the scattered light intensity and the fluorescence intensity of each particle contained in the measurement sample derived from the test blood specimen generated by the measurement unit information processing unit (Step S1).

Subsequently, the processing unit 21 compares the scattered light intensity and the fluorescence intensity of each particle contained in the measurement sample acquired in Step S1, with the value of the range of scattered light intensities and the range of fluorescence intensities preset for classifying each population of lymphocytes, monocytes, total neutrophils, and eosinophils, that are stored in the auxiliary storage unit 24. Then, the processing unit 21 classifies each particle into a lymphocyte population, a monocyte population, a total neutrophil population, and an eosinophil population (Step S11).

Next, the processing unit 21 acquires particle number information for each population based on the scattered light intensity and the fluorescence intensity (Step S12). The processing unit 21 may perform a step (not shown) of acquiring particle number information of the white blood cell population from the scattered light intensity. The acquisition of the particle number information of the white blood cell population may be made at any time as long as it is before Step S31 described later.

Subsequently, the processing unit 21 acquires particle number information of the second population which is a neutrophil population not including the first population corresponding to the control neutrophil population. At least two patterns are assumed for a method for acquiring the particle number information of the second population.

As the first pattern, the processing unit 21 compares the scattered light intensity and the fluorescence intensity of the neutrophils contained in the total neutrophil population derived from the test blood specimen, with the range of scattered light intensities and the range of fluorescence intensities of the control neutrophil population stored in the storage unit 24 (Step S13). Subsequently, the processing unit 21 determines, among the neutrophils contained in the total neutrophil population derived from the test blood specimen, a neutrophil population that is included in the range of scattered light intensities of the control neutrophil population and also included in the range of fluorescence intensities as the first population (Step S14). Then, the processing unit 21 is a method for determining a neutrophil population not including the first population among the neutrophils contained in the total neutrophil population as the second population (Step S15).

Examples of the second pattern include the following method. The processing unit 21 compares the scattered light intensity and the fluorescence intensity of neutrophils contained in the total neutrophil population derived from the test blood specimen, with the range of scattered light intensities and the range of fluorescence intensities of the control neutrophil population (Step S13). Based on the comparison result, the processing unit 21 determines, among the neutrophils contained in the total neutrophil population derived from the test blood specimen, a neutrophil population that is included in the range of scattered light intensities of the control neutrophil population and also included in the range of fluorescence intensities as the first population (Step S14). The processing unit 21 compares the fluorescence intensity of neutrophils contained in the total neutrophil population derived from the test blood specimen with the lower limit of the fluorescence intensity of the immature granulocyte population stored in the storage unit 24. The processing unit 21 determines a particle population in which the fluorescence intensity is between the lower limit of the fluorescence intensity of the immature granulocyte population and the upper limit of the fluorescence intensity of the first population, and the scattered light intensity is in the range of scattered light intensities of the first population, as the second population (not shown).

The processing unit 21 acquires particle number information of a second population not including the first population obtained in either the first pattern or the second pattern (Step S2).

Figure 8:
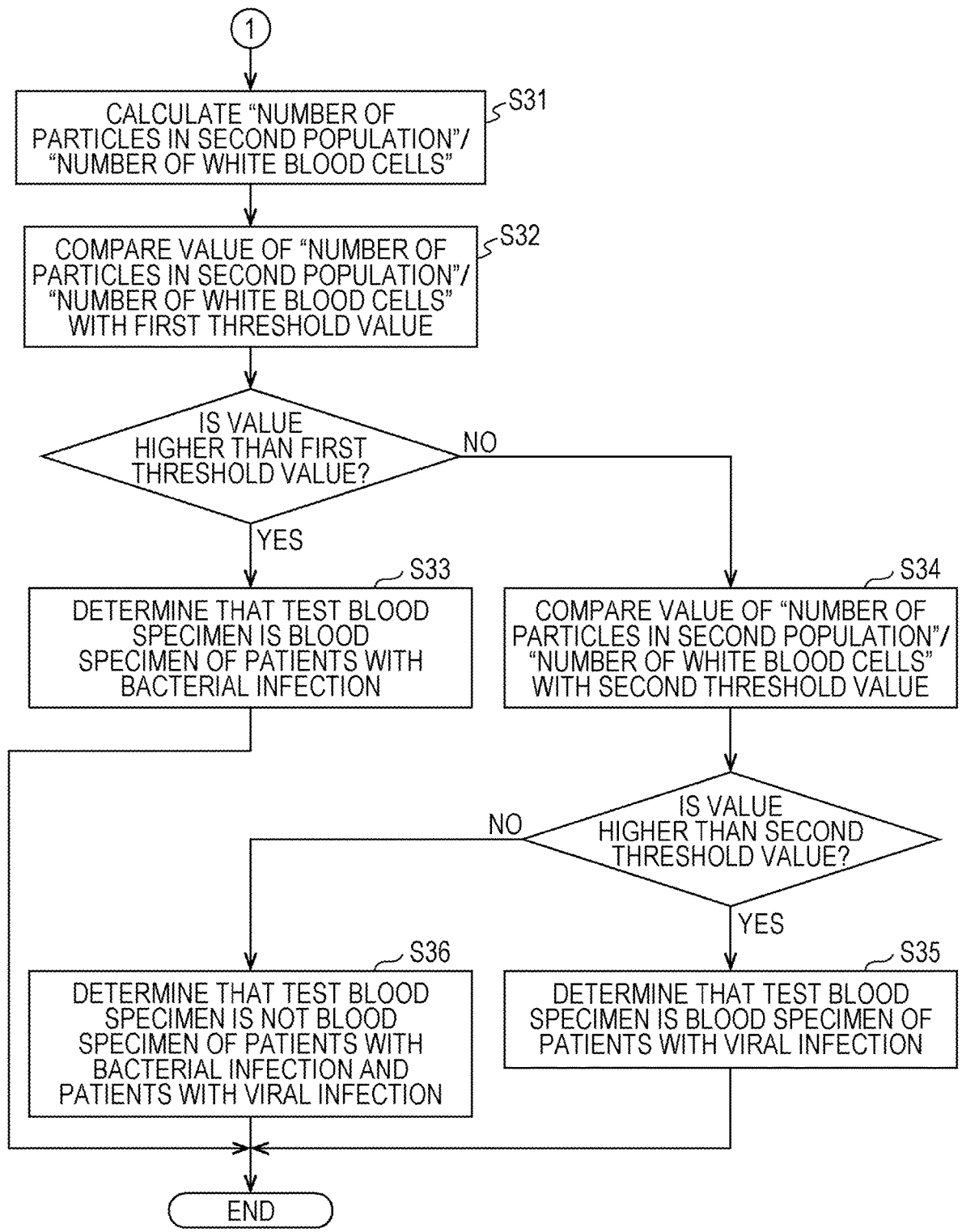
FIG. 8 is a diagram showing a part of the operations of a data processing unit continued from FIG. 7.

Further, as shown in FIG. 8, based on the particle number information of the second population acquired in Step S2, the processing unit 21 further determines whether the test blood specimen is a specimen collected from patients with bacterial infection or patients with viral infection (Step S3).

More specifically, the processing unit 21 obtains the ratio of the number of particles included in the particle number information of the second population acquired in Step S2 to the number of particles included in the particle number information of the white blood cell population acquired in Step S13 ("the number of particles in the second population"/"the number of white blood cells") (Step S31) and compares the value of "the number of particles in the second population"/"the number of white blood cells" with the preset first threshold value (Step S32). When "the number of particles in the second population"/"the number of white blood cells" is higher than the first threshold value, the processing unit 21 can determine that the test blood specimen is a specimen collected from patients with bacterial infection (Step S33). When "the number of particles in the second population"/"the number of white blood cells" is equal to or less than the first threshold value, the processing unit 21 compares "the number of particles in the second population"/"the number of white blood cells" with the second threshold value (Step S34). When "the number of particles in the second population"/"the number of white blood cells" is equal to or less than the first threshold value and is higher than the second threshold value, the processing unit 21 can determine that the test blood specimen is a specimen collected from patients with viral infection (Step S35). When "the number of particles in the second population"/"the number of white blood cells" is equal to or less than the second threshold value, the processing unit 21 can determine that the test blood specimen is not a specimen collected from patients with bacterial infection and patients with viral infection (Step S36).

The processing unit 21 may output the result obtained in the above-described Step S33, S35 or S36 from the output unit 31 or may record the result in a recording medium 32. Although not shown, the processing unit 21 may output the particle number information obtained in Step S2 from the output unit 31 or may record the particle number information in the recording medium 32.

In the second embodiment, "the number of particles in the second population"/"the number of white blood cells" can be replaced with "the number of particles in the second population"/"the number of particles in the total neutrophil population" or "the number of particles in the second population"/"the number of particles in the total lymphocyte population", as in the first embodiment.

[3. Computer Program for Particle Analysis for Identifying Infections]

The third embodiment relates to a computer program for particle analysis for identifying infections. Specifically, it is a computer program for controlling the operation of the particle analyzer for identifying infections described in 2-4. above.

Figure 7:
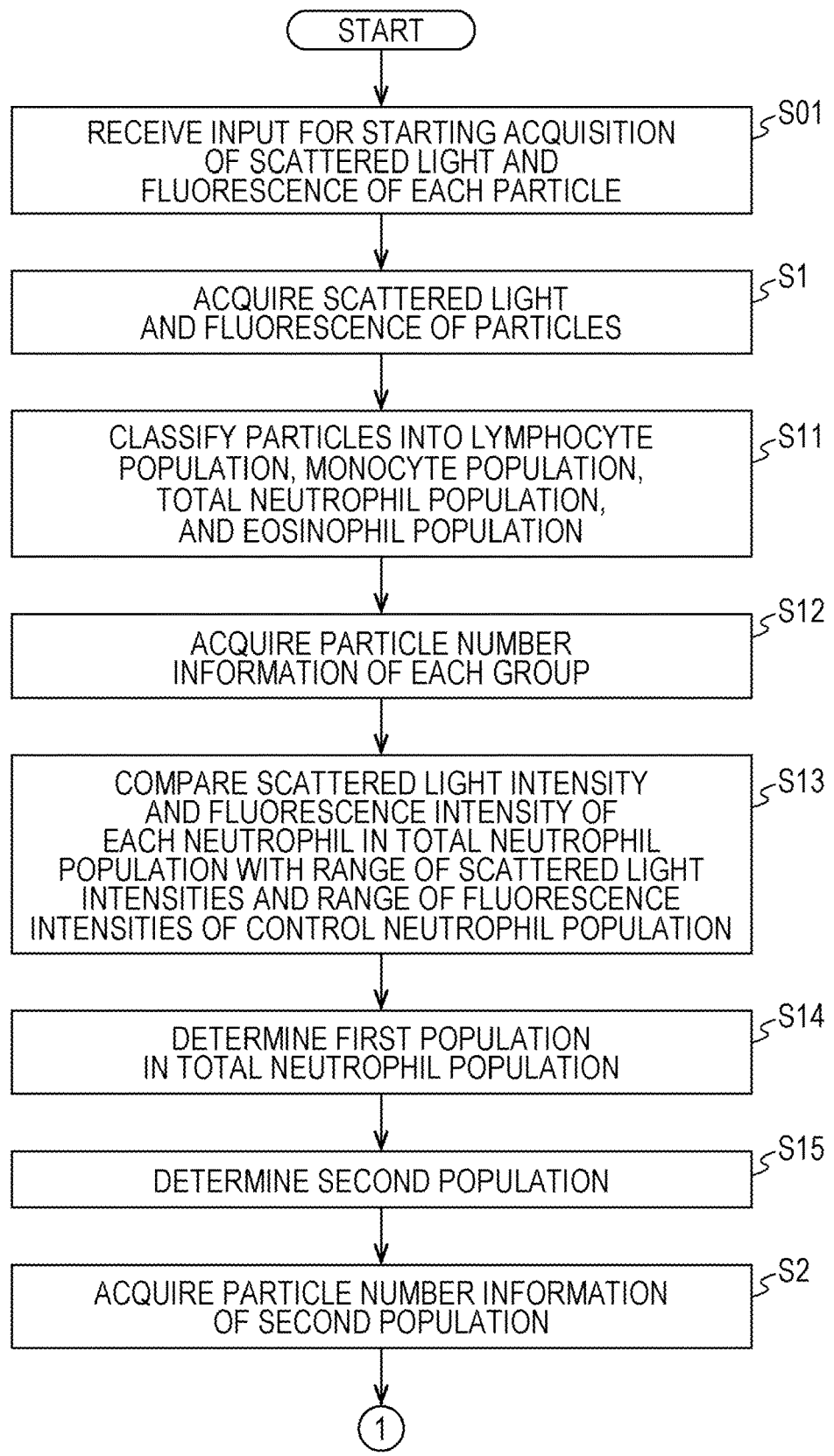
FIG. 7 is a diagram showing a part of operations of a data processing unit.

Steps executed by the computer program of the third embodiment are Steps S01, S1, S11 to S16, S16' and S2 described in FIG. 7 described in 2-4. above and Steps S31 to S35 described in FIG. 8. The description of the steps described in 2-4. above can be incorporated in the third embodiment. The explanation of each term described in the above section 1. can also be incorporated in the third embodiment.

The program according to the third embodiment may be stored in a semiconductor memory element such as a hard disk or a flash memory, or a storage medium such as an optical disk. The storage format of the program in the storage medium is not limited as long as the presentation apparatus can read the program. Storage into the storage medium is preferably nonvolatile.

While each embodiment has been described in detail with reference to the accompanying drawings, the particle analysis method for identifying infections in the present disclosure, a particle analyzer for identifying infections, and a computer program for particle analysis for identifying infections is not limited to the specific embodiments described above. Embodiments can be modified based on the description of this specification and technical common knowledge of those skilled in the art.

EXAMPLES

Hereinafter, the present disclosure will be described by way of examples, but the present disclosure is not to be construed as being limited to the examples.

1. Example 1

Peripheral blood was collected from subjects belonging to each of infectious disease groups from 01 to 05, and the number of white blood cells, and the numbers of particles of total neutrophil population, first population, and lymphocyte population per unit volume were counted by XN-1000 (SYSMEX CORPORATION). The definitive diagnosis of each infectious disease was made by a doctor based on a conventional infectious disease test such as PCR test.

01_Dengue fever (virus) n=82
02_Chikungunya fever (virus) n=7
03_Typhoid (bacteria) n=8
04_Leptospira (bacteria) n=5
05_Bacteremia (bacteria): very severe n=9

The number of particles in the second population not including the first population was obtained by subtracting the number of particles in the first population from the number of particles in the total neutrophil population for the peripheral blood of each subject.

Figure 9:
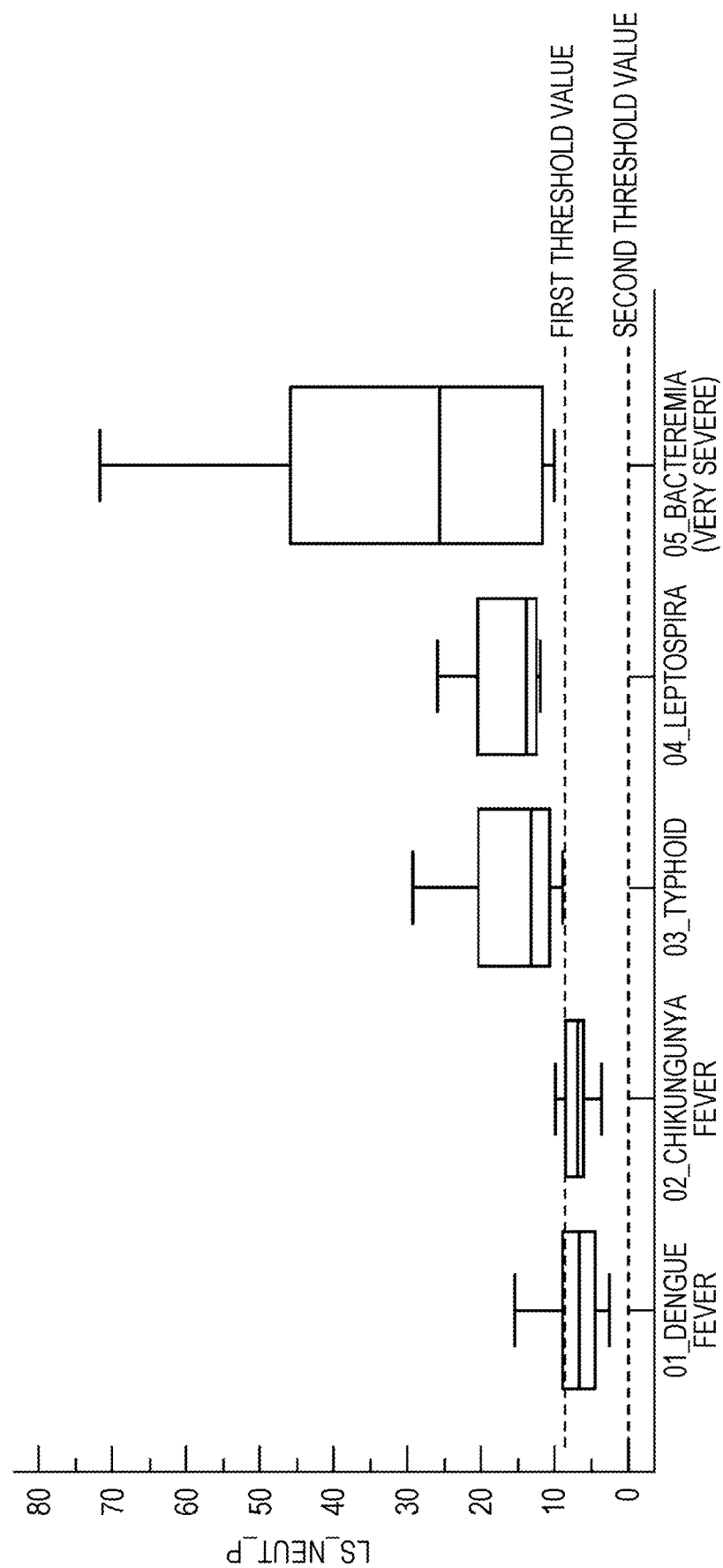
FIG. 9 is a diagram showing distributions of LS_LEUT_P values for each of infectious disease groups from 01 to 05.

For each peripheral blood, the value obtained by dividing "the number of particles in the second population" by "the number of white blood cells" was multiplied by 100 to obtain LS_LEUT_P values. The distributions of the LS_LEUT_P values of each of infectious disease groups are shown in FIG. 9.

Between three groups of the 03_typhoid group, the 04_leptospira group, and the 05_bacteremia group, and two groups of the 01_dengue fever group and the 02_chikungunya fever group, which are blood specimens of patients with bacterial infection, the threshold value could be set at 9.8 for the LS_LEUT_P values, by the discriminant analysis method of the 2 groups.

2. Comparative Example

Figure 10:
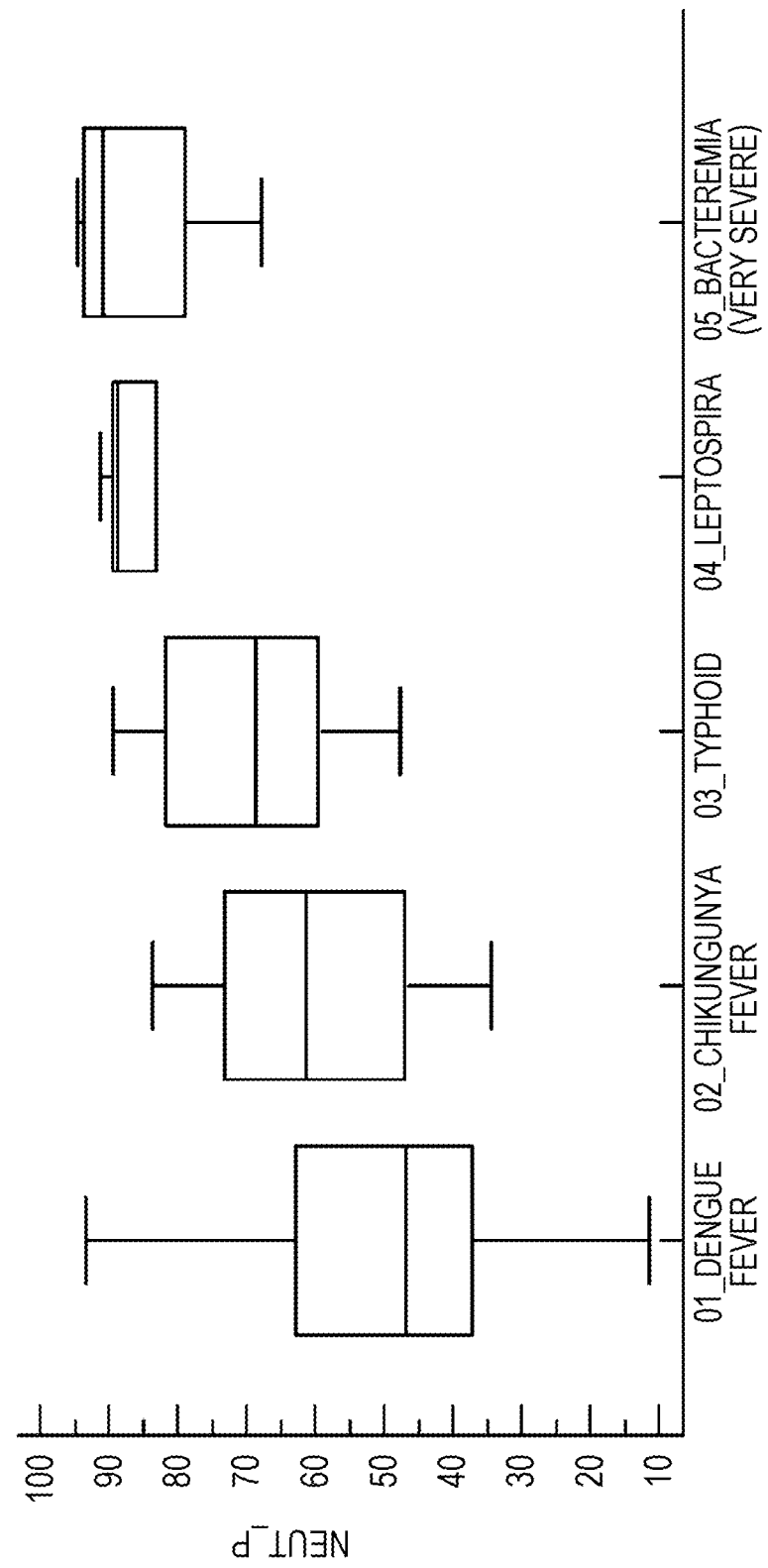
FIG. 10 is a diagram showing distributions of LEUT_P values for each of infectious disease groups from 01 to 05.

For each of infectious disease groups from 01 to 05 above, the value obtained by dividing "the number of particles in the total neutrophil population" by "the number of white blood cells" was multiplied by 100 to obtain LEUT_P values. The distributions of the LEUT_P values of each of groups are shown in FIG. 10.

In the LEUT_P values, a significant difference was not found between three groups of the 03_typhoid group, the 04_leptospira group, and the 05_bacteremia group, and two groups of the 01_dengue fever group and the 02_chikungunya fever group, and the threshold value could not be set.

Based on the above results, it was considered that the LS_LEUT_P values could identify blood specimens from patients with bacterial infection and blood specimens from patients with viral infection.

What is claimed is:

1. A particle analysis method for identifying infection, comprising:
   step A of irradiating light on a measurement sample prepared by mixing a test blood specimen comprising particles, collected from a subject, a fluorescent dye that stains a nucleic acid, and a hemolytic agent, thereby acquiring scattered light and fluorescence from each particle comprised in the measurement sample,
   step B of specifying particles that are substantially not comprised in blood of control subjects not suffering from infection and are determined to be neutrophils comprised in blood of patients with infection, based on the scattered light and the fluorescence, and acquiring particle number information on the specified particles, and
   step C of determining whether the test blood specimen is a specimen collected from patients with bacterial infection or a specimen collected from patients with viral infection, based on the particle number information.

2. The method according to claim 1, wherein
   in the step A, scattered light intensity and fluorescence intensity are acquired based on the scattered light and the fluorescence, and
   in the step B, the particles are specified based on the scattered light intensity and the fluorescence intensity.

3. The method according to claim 1, comprising, between the step A and the step B, step A-1 of acquiring particle number information of total neutrophil population and particle number information of first population, from the scattered light and the fluorescence acquired in the step A, wherein
   the first population is a particle population determined to correspond to a neutrophil population comprised in the blood of control subjects not suffering from infection in the measurement sample, and
   the particles specified in the step B are particles comprised in the total neutrophil population and not comprised in the first population.

4. The method according to claim 3, wherein the particle population determined to be a neutrophil population comprised in the blood of control subjects not suffering from infection is a particle population comprised within the range of scattered light intensities and within the range of fluorescence intensities preset using a control blood specimen collected from the control subjects.

5. The method according to claim 1, wherein the control subject is a person whose ratio of band neutrophils in white blood cells comprised in the blood does not exceed a reference value.

6. The method according to claim 3, wherein the particles specified in the step (B)
   appear at a position where the fluorescence intensity is lower than an appearance position of immature granulocyte population,
   appear at a position where the fluorescence intensity is higher than that of the first population, and
   appear in substantially the same range of scattered light intensities as the first population.

7. The method according to claim 3, wherein the step C is a step of determining whether the test blood specimen is a specimen collected from patients with bacterial infection or a specimen collected from patients with viral infection, based on a ratio of the number of particles comprised in the particle number information of a total neutrophil population to the number of particles comprised in the particle number information acquired in the step B.

8. The method according to claim 3, further comprising a step of acquiring particle number information of a white blood cell population in the measurement sample before the step C,
   wherein the step C is a step of determining whether the test blood specimen is a specimen collected from patients with bacterial infection or a specimen collected from patients with viral infection, based on a ratio of the number of particles comprised in the particle number information of the white blood cell population to the number of particles comprised in the particle number information acquired in the step B.

9. The method according to claim 8, wherein the step C is a step of calculating a ratio of the number of particles acquired in the step B to the number of particles of white blood cell population, comparing the ratio with a first threshold value, and when the ratio is higher than the first threshold value, determining that the test blood specimen is a specimen collected from patients with bacterial infection.

10. The method according to claim 9, wherein the step C is a step of comparing the ratio with a second threshold value which is lower than the first threshold value, and when the ratio is equal to or less than the first threshold value and higher than the second threshold value, determining that the test blood specimen is a specimen collected from patients with viral infection.

11. The method according to claim 10, wherein the step C is a step of, when the ratio is equal to or less than the second threshold value, determining that the test blood specimen is a specimen collected from a subject not infected by either virus or bacterium.

12. A particle analyzer for identifying infections, comprising: a light source for irradiating light on a measurement sample prepared by mixing a test blood specimen comprising particles, collected from a subject, a fluorescent dye that stains a nucleic acid, and a hemolytic agent, a detection unit for receiving scattered light and fluorescence from each particle comprised in the measurement sample generated by the irradiation, and a processing unit programmed for specifying particles that are substantially not comprised in blood of control subjects not suffering from infection and are determined to be neutrophils comprised in blood of patients with infection, based on the scattered light and the fluorescence, and acquiring particle number information on the specified particles, and further programmed for determining whether the test blood specimen is a specimen collected from patients with bacterial infection or a specimen collected from patients with viral infection, based on the particle number information.

13. The analyzer according to claim 12, wherein the processing unit
   acquires scattered light intensity and fluorescence intensity from scattered light and fluorescence received by the detection unit, and
   specifies particles that are not substantially comprised in the blood of control subjects not suffering from infection and are determined to be neutrophils comprised in the blood of patients with infection, based on the scattered light intensity and the fluorescence intensity.

14. The analyzer according to claim 12, wherein the processing unit
   further acquires particle number information of a total neutrophil population and particle number information of a first population, based on the scattered light and the fluorescence, and
   the first population is a particle population determined to correspond to a neutrophil population comprised in the blood of control subjects not suffering from infection in the test blood specimen.

15. The analyzer according to claim 14, further comprising a storage unit for storing information on the scattered light intensity range and the fluorescence intensity range for determining the first population, and information on the scattered light intensity range and the fluorescence intensity range for determining the total neutrophil population,
   wherein the processing unit
   compares scattered light intensity and fluorescence intensity of each particle in the measurement sample with the information of the scattered light intensity range and the fluorescence intensity range stored in the storage unit,
   determines a first population in the measurement sample and a total neutrophil population based on the comparison result, and
   specifies particles comprised in the total neutrophil population and not comprised in the first population as particles substantially not comprised in the blood of the control subject not suffering from infection and determined to be neutrophils comprised in the blood of patients with infection.

16. The analyzer according to claim 12, wherein the processing unit
   further acquires particle number information of the white blood cell population in the measurement sample.

17. The analyzer according to claim 16, wherein the processing unit
   calculates a ratio of the number of particles comprised in the particle number information of the white blood cell population to the number of particles substantially not comprised in blood of the control subject not suffering from infection and determined to be neutrophils comprised in blood of patients with infection, and compares the ratio with a first threshold value, and when the ratio is higher than the first threshold value, determines that the test blood specimen is a specimen collected from patients with bacterial infection.

18. The analyzer according to claim 17, wherein the processing unit compares the ratio with a second threshold value which is lower than the first threshold value, and when the ratio is equal to or less than the first threshold value and higher than the second threshold value, determines that the test blood specimen is a specimen collected from patients with viral infection.

19. The analyzer according to claim 18, wherein the processing unit,
determines that the test blood specimen is a specimen collected from a subject not infected by either virus or bacterium when the ratio is equal to or less than the second threshold value.

20. A particle analyzer for identifying infections, comprising: a light source for irradiating light on a measurement sample prepared by mixing a test blood specimen comprising particles, collected from a subject, a fluorescent dye that stains a nucleic acid, and a hemolytic agent, a detection unit for receiving scattered light and fluorescence from each particle comprised in the measurement sample generated by the irradiation, and a processing unit programmed for specifying particles that are substantially not comprised in blood of control subjects not suffering from infection and are determined to be neutrophils comprised in blood of patients with infection, based on the scattered light and the fluorescence, and acquiring particle number information on the specified particles, outputting the particle number information, and further programmed for determining whether the test blood specimen is a specimen collected from patients with bacterial infection or a specimen collected from patients with viral infection.

* * * * *